(12) United States Patent
Nivens

(10) Patent No.: US 11,369,387 B2
(45) Date of Patent: Jun. 28, 2022

(54) TOURNIQUET ASSEMBLY

(71) Applicant: Eric Nivens, Las Vegas, NV (US)

(72) Inventor: Eric Nivens, Las Vegas, NV (US)

( * ) Notice: Subject to any disclaimer, the term of this patent is extended or adjusted under 35 U.S.C. 154(b) by 140 days.

(21) Appl. No.: 16/892,518

(22) Filed: Jun. 4, 2020

(65) Prior Publication Data
US 2021/0378682 A1    Dec. 9, 2021

(51) Int. Cl.
*A61B 17/132*    (2006.01)

(52) U.S. Cl.
CPC ................. *A61B 17/1322* (2013.01)

(58) Field of Classification Search
CPC .............. A61B 17/132; A61B 17/1322; A61B 17/1325; A61F 2013/00102; A61F 2013/0028
USPC ............................................ 602/75; D24/189
See application file for complete search history.

(56) References Cited

U.S. PATENT DOCUMENTS

| | | | | |
|---|---|---|---|---|
| 268,407 A * | 12/1882 | Hughes | ............... | A61B 17/1327 606/203 |
| 2,706,476 A * | 4/1955 | Diamond | ............... | A61F 13/063 128/889 |
| 2,858,830 A * | 11/1958 | Robins | .................. | A61F 13/105 604/307 |
| 2,868,193 A * | 1/1959 | Kreft | ................. | A61F 13/00034 602/6 |
| 3,026,874 A * | 3/1962 | Stevens | ................... | A61M 1/90 604/305 |
| 3,050,064 A * | 8/1962 | Moore | ............... | A61B 17/1325 606/203 |
| 3,122,141 A * | 2/1964 | Crowe, Jr. | ............ | A61L 15/425 604/369 |
| 3,171,410 A * | 3/1965 | Towle, Jr. | ......... | A61F 13/00068 602/53 |
| 3,789,842 A * | 2/1974 | Froimson | ............... | A61F 15/006 602/62 |
| 3,954,109 A * | 5/1976 | Patel | .................. | A61B 17/1325 606/203 |
| 4,534,354 A * | 8/1985 | Bonner, Jr | ......... | A41D 13/0568 607/108 |
| 4,693,241 A * | 9/1987 | Trznadel | ............... | A61F 13/062 602/62 |
| 5,201,758 A | 4/1993 | Glover | | |
| 5,411,518 A | 5/1995 | Goldstein | | |
| 5,423,736 A * | 6/1995 | Cartmell | ............... | A61B 17/085 602/42 |
| 5,507,721 A * | 4/1996 | Shippert | ........... | A61F 13/00034 602/46 |

(Continued)

FOREIGN PATENT DOCUMENTS

WO    WO2001013801      3/2001

*Primary Examiner* — Ryan J. Severson

(57) ABSTRACT

A tourniquet assembly for providing additional comfort when giving blood includes a pad which is comprised of a flexible material. The pad has a first side, a second side and a perimeter edge extending between the first and second sides. The perimeter edge includes a front edge, a rear edge, a first lateral edge and a second lateral edge. The pad is elongated and has a longitudinal axis extending through the first and second lateral edges. A band is coupled to the second side of the pad. The band extends along the longitudinal axis. The band is comprised of a flexible material and is wrapped around a limb to secure the pad to a person's limb.

14 Claims, 4 Drawing Sheets

(56) References Cited

U.S. PATENT DOCUMENTS

| | | | |
|---|---|---|---|
| 5,690,610 A * | 11/1997 | Ito | A61B 17/1325 602/53 |
| 5,690,672 A | 11/1997 | Cohen | |
| 5,873,890 A * | 2/1999 | Porat | A61B 17/1325 606/201 |
| 6,189,538 B1 * | 2/2001 | Thorpe | A61B 17/1325 128/898 |
| 6,537,298 B2 | 3/2003 | Dedo | |
| 6,593,508 B1 * | 7/2003 | Harder | A61F 13/00 602/53 |
| 6,849,057 B2 * | 2/2005 | Satou | A61F 13/0273 602/75 |
| 7,329,792 B2 * | 2/2008 | Buckman | A61F 13/00 602/42 |
| 7,527,602 B2 * | 5/2009 | Weaver, II | A61F 13/108 602/20 |
| 8,628,488 B2 * | 1/2014 | Serola | A61F 5/024 602/75 |
| 9,271,877 B2 * | 3/2016 | Mouton | A61F 13/069 |
| 10,092,297 B2 * | 10/2018 | Hoff | A61B 17/1325 |
| 10,456,559 B2 * | 10/2019 | Wilborn | A61F 13/0269 |
| 11,033,280 B2 * | 6/2021 | Hoff | A61B 17/1325 |
| 2002/0188315 A1 | 12/2002 | Guzman | |
| 2003/0229375 A1 * | 12/2003 | Fleischer | A61B 17/1325 606/201 |
| 2004/0092999 A1 * | 5/2004 | Lojewski | A61B 17/1325 606/185 |
| 2007/0185428 A1 * | 8/2007 | Harder | A61F 15/00 602/75 |
| 2007/0282234 A1 * | 12/2007 | Rynd | A61F 15/004 602/41 |
| 2008/0262479 A1 * | 10/2008 | Barela | A61B 17/132 606/1 |
| 2008/0269659 A1 * | 10/2008 | Bergin | A61B 17/0057 602/49 |
| 2012/0053617 A1 * | 3/2012 | Benz | A61B 17/1327 606/203 |
| 2012/0232579 A1 * | 9/2012 | Lee | A61F 5/30 606/202 |
| 2013/0237866 A1 * | 9/2013 | Cohen | A61B 5/445 600/502 |
| 2014/0135819 A1 * | 5/2014 | Brown | A61B 17/1327 606/203 |
| 2015/0305958 A1 * | 10/2015 | Hoff | A61B 17/1325 601/134 |
| 2019/0099188 A1 * | 4/2019 | Hoff | A61B 17/1325 |
| 2021/0378682 A1 * | 12/2021 | Nivens | A61B 17/1322 |

* cited by examiner

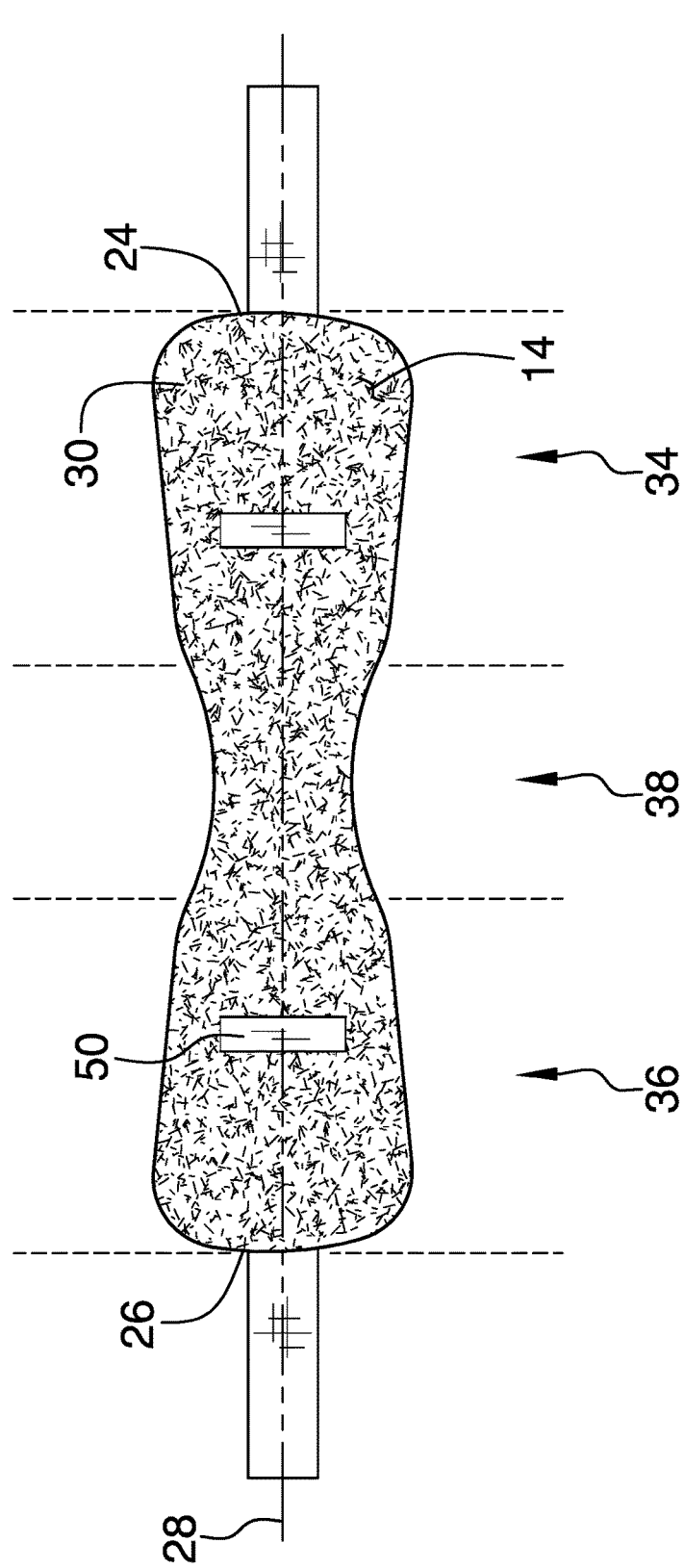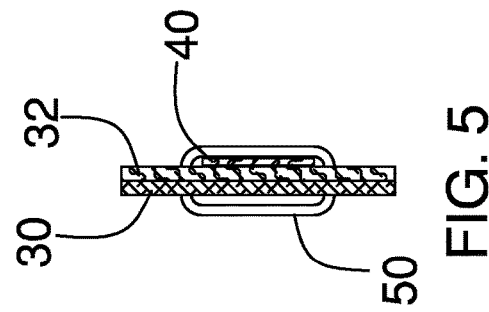

TOURNIQUET ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to tourniquet devices and more particularly pertains to a new tourniquet device for providing additional comfort for the wearer of the tourniquet. The pad has an increased surface area to provide for additional comfort to the person on which the tourniquet is applied.

(2) Description of Related Art Including Information Disclosed Under 37 CFR 1.97 and 1.98

The prior art relates to tourniquet devices having improved comfort attributes and which include, for example, inflatable bladders to improve comfort to the user.

BRIEF SUMMARY OF THE INVENTION

An embodiment of the disclosure meets the needs presented above by generally comprising a pad which is comprised of a flexible material. The pad has a first side, a second side and a perimeter edge extending between the first and second sides. The perimeter edge includes a front edge, a rear edge, a first lateral edge and a second lateral edge. The pad is elongated and has a longitudinal axis extending through the first and second lateral edges. A band is coupled to the second side of the pad. The band extends along the longitudinal axis. The band is comprised of a flexible material and is configured to wrap around a limb to secure the pad to a person's limb.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 3 is a front view of an embodiment of the disclosure.

FIG. 5 is a cross-sectional view of an embodiment of the disclosure taken along line 5-5 of FIG. 2.

DETAILED DESCRIPTION OF THE INVENTION

Figure 1:
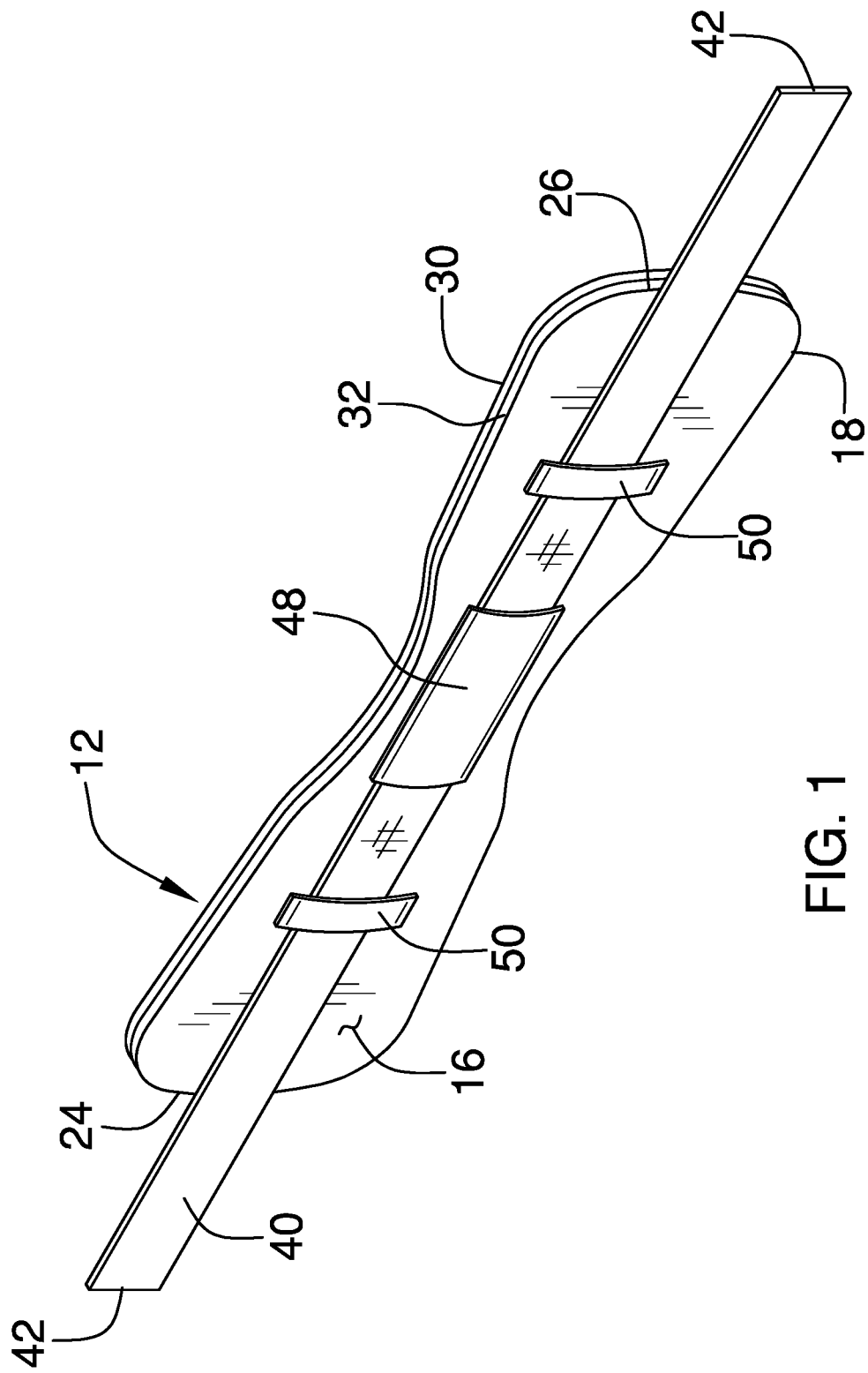
FIG. 1 is a rear isometric view of a tourniquet assembly according to an embodiment of the disclosure.
Figure 2:
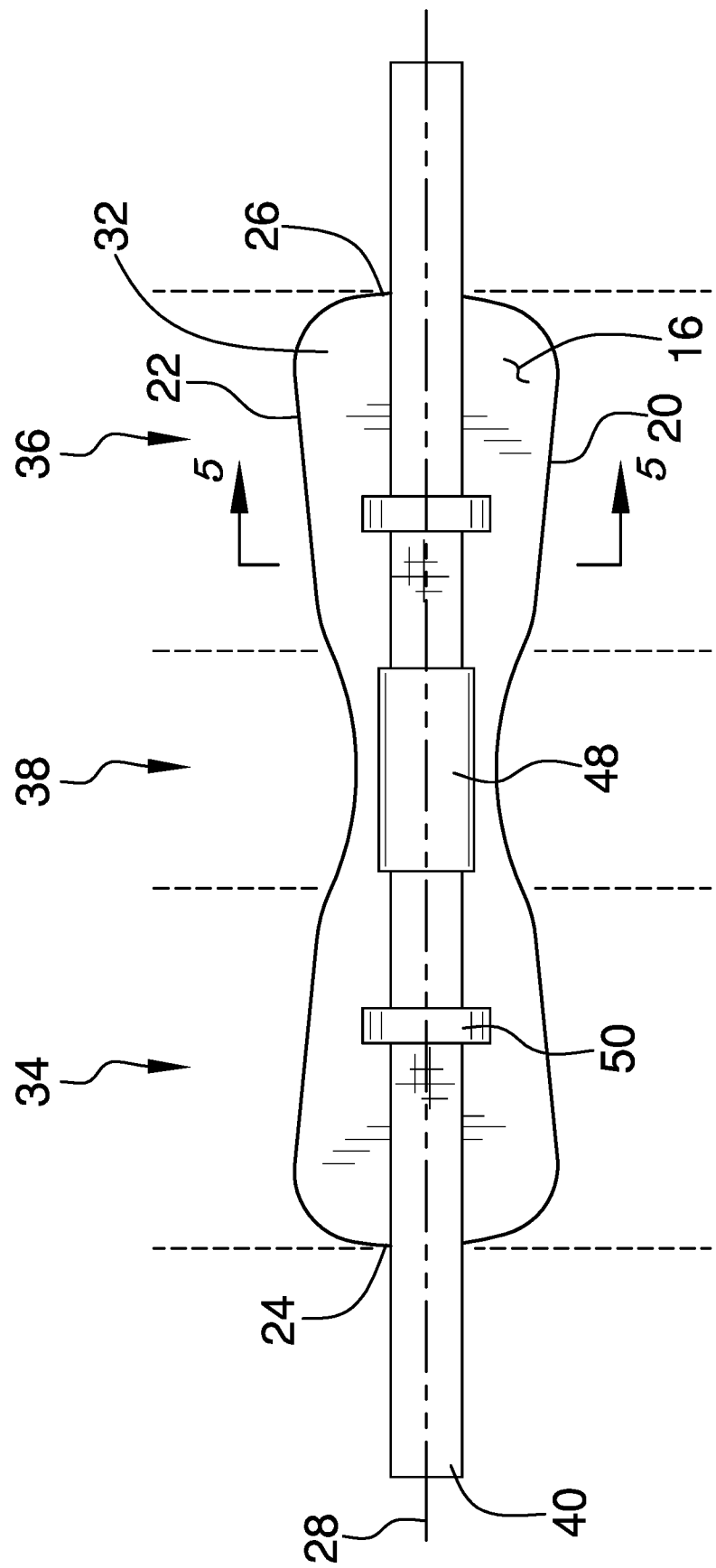
FIG. 2 is a rear view of an embodiment of the disclosure.
Figure 4:
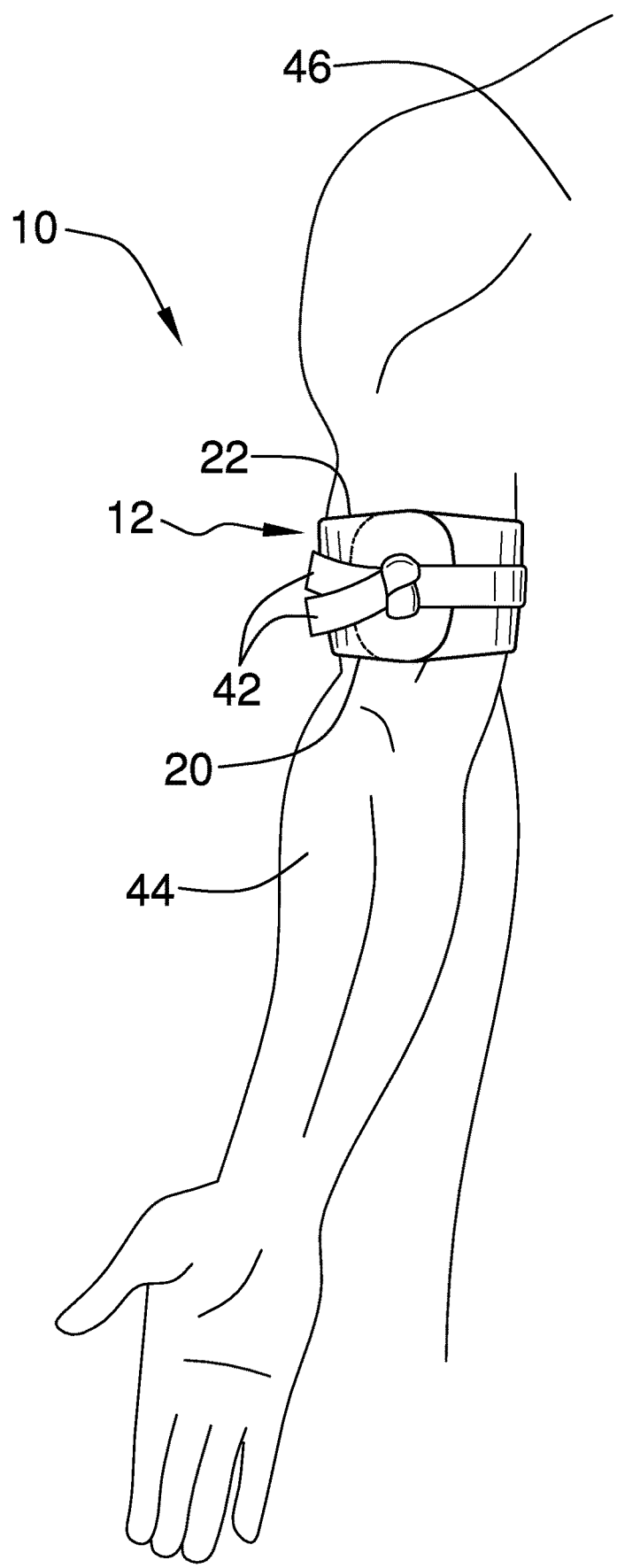
FIG. 4 is an in-use view of an embodiment of the disclosure.

With reference now to the drawings, and in particular to FIGS. 1 through 5 thereof, a new tourniquet device embodying the principles and concepts of an embodiment of the disclosure and generally designated by the reference numeral 10 will be described.

As best illustrated in FIGS. 1 through 5, the tourniquet assembly 10 generally comprises a pad 12 which is comprised of a flexible material. The pad 12 has a first side 14, a second side 16 and a perimeter edge 18 extending between the first side 14 and second side 16. The perimeter edge 18 includes a front edge 20, a rear edge 22, a first lateral edge 24 and a second lateral edge 26. The pad 12 is elongated and has a longitudinal axis 28 extending through the first lateral edge 24 and second lateral edge 26. The pad 12 is comprised of a plurality of layers. The plurality of layers include at least an inner layer 30 including the first side 14 and an outer layer 32 including the second side 16. The plurality of layers is non-removably attached to each other.

The first side 14 is completely comprised of the inner layer 30. The inner layer 30 is comprised of a cloth material. The cloth material may be comprised of natural and/or synthetic materials which may be woven, fibrous bunched, compressed, or formed by any other conventional methods of cloth manufacture. The inner layer 30 may be comprised of many individual layers of the cloth material. The second side 16 is completely comprised of the outer layer 32. The outer layer 32 may be comprised of an elastomeric material. Suitable elastomeric materials include synthetic rubber, neoprene, nitrile, and other conventionally available materials, and which may specifically include non-latex elastomeric materials. The inner layer 30 and the outer layer 32 are both comprised of a non-latex material. The pad 12 includes a first portion 34 including the first lateral edge 24, a second portion 36 including the second lateral edge 26 and a central portion 38 positioned between the first portion 34 and second portion 36.

A band 40 is coupled to the second side 16 of the pad 12. The band 40 extends along the longitudinal axis 28 and has a pair of free ends 42. The band 40 is comprised of a flexible material and is configured to wrap around a limb 44 to secure the pad 12 to a person's 46 limb 44. Suitable flexible materials include cloths, elastomeric materials, plastics, and other conventional materials capable of being wrapped around the limb 44. A sleeve 48 is attached to the second side 16 of the pad 12. The sleeve 48 is located on the central portion 38 of the pad 12. The band 40 extends through the sleeve 48 such that the band 40 is attached to the pad 12. A plurality of loops 50 is attached to the second side 16 of the pad 12 and is aligned with the sleeve 48 such that the band 40 extends between each of the loops 50 and the pad 12. Each of the first portion 34 and second portion 36 has at least one of the loops 50 attached thereto. The sleeve 48 and loops 50 are comprised of a non-latex material.

The first portion 34 and second portion 36 have a greater width from the front edge 20 to the rear edge 22 than a width of the central portion 38. The greater width of the first portion 34 and second portion 36 is between 1.50 inches and 4.00 inches. The width of the central portion 38 is between 1.00 inch and 2.50 inches. Each of the first portion 34 and second portion 36 has a same shape with respect to each other. The first portion 34 and second portion 36 each have a length between 2.50 inches and 6.00 inches. The central portion 38 has a length between 2.00 and 4.00 inches.

In use, the pad 12 is placed onto the limb 44 with the inner layer 30 in contact with the limb 44 and the front edge 20 orientated away from the person 46. The first lateral edge 24 and the second lateral edge 26 are wrapped around the limb 44. The free ends 42 of the strap 40 are wrapped along the outer layer 16 around the limb 44 and secured to each other to secure the pad 12 in place.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A padded tourniquet assembly comprising:
    a pad being comprised of a flexible material, said pad having a first side, a second side and a perimeter edge extending between said first and second sides, said perimeter edge including a front edge, a rear edge, a first lateral edge and a second lateral edge, said pad being elongated and having a longitudinal axis extending through said first and second lateral edges;
    a band being coupled to said second side of said pad, said band extending along said longitudinal axis, said band being comprised of a flexible material and being configured to wrap around a limb to secure said pad to a person's limb;
    a sleeve is attached to said second side of said pad, said band extending through said sleeve such that said band is attached to said pad; and
    a plurality of loops attached to said second side of said pad and is aligned with said sleeve such that said band extends between each of said loops and said pad.

2. The padded tourniquet assembly according to claim 1, wherein said pad is comprised of a plurality of layers, said plurality of layers including an inner layer including said first side and an outer layer including said second side.

3. The padded tourniquet assembly according to claim 2, wherein said plurality of layers is non-removably attached to each other.

4. The padded tourniquet assembly according to claim 3, wherein said first side is completely comprised of said inner layer.

5. The padded tourniquet assembly according to claim 4, wherein said inner layer is comprised of a cloth material.

6. The padded tourniquet assembly according to claim 5, wherein said inner layer is free of latex material.

7. The padded tourniquet assembly according to claim 5, wherein said outer layer is free of latex material.

8. The padded tourniquet assembly according to claim 1, wherein said pad includes a first portion including said first lateral edge, a second portion including said second lateral edge and a central portion positioned between said first and second portions.

9. The padded tourniquet assembly according to claim 1, wherein said band has a pair of free ends.

10. The padded tourniquet assembly according to claim 1, wherein said sleeve is located on said central portion of said pad.

11. A padded tourniquet assembly comprising:
    a pad being comprised of a flexible material, said pad having a first side, a second side and a perimeter edge extending between said first and second sides, said perimeter edge including a front edge, a rear edge, a first lateral edge and a second lateral edge, said pad being elongated and having a longitudinal axis extending through said first and second lateral edges, said pad including a first portion including said first lateral edge, a second portion including said second lateral edge and a central portion positioned between said first and second portions;
    a band being coupled to said second side of said pad, said band extending along said longitudinal axis, said band being comprised of a flexible material and being configured to wrap around a limb to secure said pad to a person's limb;
    a sleeve attached to said second side of said pad, said band extending through said sleeve such that said band is attached to said pad, said sleeve being located on said central portion of said pad; and
    wherein a plurality of loops is attached to said second side of said pad and is aligned with said sleeve such that said band extends between each of said loops and said pad, each of said first and second portions having at least one of said loops attached thereto.

12. The padded tourniquet assembly according to claim 11, wherein said first and second portions have a greater width from said front edge to said rear edge than a width of said central portion, each of said first and second portions having the same shape with respect to each other.

13. The padded tourniquet assembly according to claim 12, said first and second portions each has a length between 2.50 inches and 6.00 inches, said central portion having a length between 2.00 and 4.00 inches.

14. A padded tourniquet assembly comprising:

a pad being comprised of a flexible material, said pad having a first side, a second side and a perimeter edge extending between said first and second sides, said perimeter edge including a front edge, a rear edge, a first lateral edge and a second lateral edge, said pad being elongated and having a longitudinal axis extending through said first and second lateral edges;

said pad being comprised of a plurality of layers, said plurality of layers including an inner layer including said first side and an outer layer including said second side, said plurality of layers being non-removably attached to each other, said first side being completely comprised of said inner layer, said inner layer being comprised of a cloth material, said inner and outer layers being is free of latex material;

said pad including a first portion including said first lateral edge, a second portion including said second lateral edge and a central portion positioned between said first and second portions;

a band being coupled to said second side of said pad, said band extending along said longitudinal axis, said band having a pair of free ends, said band being comprised of a flexible material and being configured to wrap around a limb to secure said pad to a person's limb;

a sleeve being attached to said second side of said pad, said band extending through said sleeve such that said band is attached to said pad, said sleeve being located on said central portion of said pad;

a plurality of loops being attached to said second side of said pad and being aligned with said sleeve such that said band extends between each of said loops and said pad, each of said first and second portions having at least one of said loops attached thereto; and said first and second portions having a greater width from said front edge to said rear edge than a width of said central portion, each of said first and second portions having a same shape with respect to each other, said first and second portions each having a length between 2.50 inches and 6.00 inches, said central portion having a length between 2.00 and 4.00 inches.

* * * * *